United States Patent [19]

Pujado et al.

[11] 4,423,251

[45] Dec. 27, 1983

[54] PROCESS EMPLOYING SEQUENTIAL ISOBUTYLENE HYDRATION AND ETHERIFICATION

[75] Inventors: Peter R. Pujado, Palatine; Bipin V. Vora, Elk Grove Village, both of Ill.

[73] Assignee: UOP Inc., Des Plaines, Ill.

[21] Appl. No.: 416,414

[22] Filed: Sep. 9, 1982

[51] Int. Cl.$^3$ .................... C07C 41/06; C07C 29/04
[52] U.S. Cl. .................................. 568/697; 568/895; 568/899; 585/639; 585/654; 585/655; 585/737; 585/738
[58] Field of Search ............... 568/697, 895, 899; 585/639, 654, 655, 737, 738

[56] References Cited

U.S. PATENT DOCUMENTS

| | | | |
|---|---|---|---|
| 3,726,942 | 4/1973 | Louder | 568/697 |
| 4,329,516 | 5/1982 | Al-Muddarris | 568/697 |
| 4,334,890 | 6/1982 | Kochar et al. | 568/697 |

*Primary Examiner*—Howard T. Mars
*Assistant Examiner*—Bruce Gray
*Attorney, Agent, or Firm*—James R. Hoatson, Jr.; John F. Spears, Jr.; William H. Page, II

[57] ABSTRACT

A hydrocarbon conversion process is disclosed which may be used to produce high purity isobutylene and/or tertiary butyl alcohol and methyl tertiary butyl ether. A mixed $C_4$ feed stream is divided into two portions with a first portion being passed through a hydration zone to produce the tertiary butyl alcohol. The remaining hydrocarbons withdrawn from the hydration zone and the second portion of the feed stream are changed to an etherification zone. The unconverted hydrocarbons exiting the etherification zone may be subjected to isomerization and/or dehydrogenation to produce additional isobutylene. The high purity isobutylene is obtained by dehydrating the tertiary butyl alcohol.

15 Claims, 1 Drawing Figure

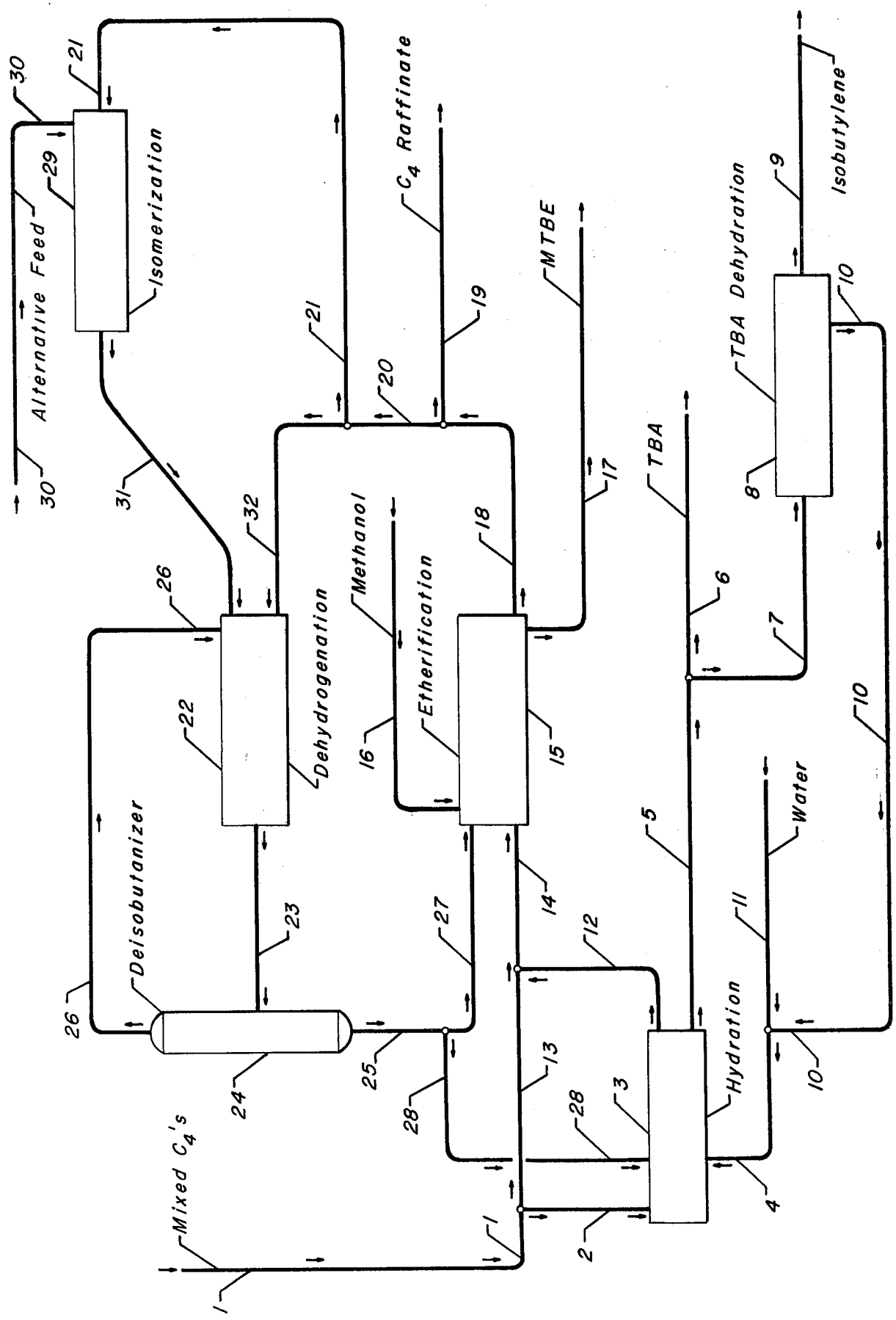

PROCESS EMPLOYING SEQUENTIAL ISOBUTYLENE HYDRATION AND ETHERIFICATION

FIELD OF THE INVENTION

The invention relates to a process for the purification and conversion of isobutylene which is present as one component of a multicomponent feed stream. The invention is an integrated hydrocarbon conversion process wherein a portion of the isobutylene present in the feed stream is consumed in a hydration zone to produce tertiary butyl alcohol and the remainder of the isobutylene is consumed in an etherification zone by reaction with an alcohol. The invention therefore relates to the conversion of isobutylene into chemical compounds useful as chemical intermediates and as motor fuel blending components. The invention also relates to methods of separating isobutylene from a mixed $C_4$ stream by selective reaction followed by dissociation of the reaction products, as by hydration to tertiary butyl alcohol followed by dehydration.

PRIOR ART

Both the hydration of isobutylene and the etherification of isobutylene are well documented petrochemical processes. For instance, the hydration of isobutylene to produce tertiary butyl alcohol is described in detail in U.S. Pat. Nos. 3,328,471 and 4,307,257. The etherification of isobutylene is described in U.S. Pat. Nos. 4,182,913; 4,219,678 and 4,282,389, with the preferred reaction being the production of methyl tertiary butyl ether.

An integrated process in which both an etherification zone and a hydration zone are employed is shown in U.S. Pat. No. 3,912,463. The process of this reference differs from the subject process in that the etherification (etheration) zone precedes the hydration zone and in that all of the hydrocarbon feed mixture flows through both zones. The hydration zone is utilized to produce secondary alcohols from linear olefins.

The separation of isobutylene from a mixture of $C_4$ hydrocarbons by etherification and the subsequent recovery of high purity isobutylene is shown in U.S. Pat. No. 4,287,379 and in an article starting at page 95 of the March, 1981 edition of *Hydrocarbon Processing*.

Processes for the dehydration of tertiary butyl alcohol to yield isobutylene are also well known. They are described in some detail in U.S. Pat. Nos. 3,510,538 and 4,155,945.

U.S. Pat. No. 4,320,232 is pertinent for its showing of a process which utilizes etherification to simultaneously produce high purity isobutylene and methyl tertiary butyl ether. The isobutylene is however produced by the decomposition of $C_3$ or $C_4$ alkyl tertiary butyl ethers. The process does not employ a hydration step and the $C_4$ feed stream is not split between separate reaction zones as in the subject process.

It is also known to integrate butane isomerization and butane dehydrogenation zones with an etherification zone. In these integrated processes isobutane and normal butane are recycled to yield increased amounts of isobutylene. This is shown in U.S. Pat. No. 4,118,425 and in articles appearing at page 91 of the Oct., 1980 edition of *Hydrocarbon Processing* and at page 191 of the Nov. 10, 1980 edition of the *Oil and Gas Journal*.

BRIEF SUMMARY OF THE INVENTION

The invention provides an improved process for producing tertiary butyl alcohol and an ether from the isobutylene present in an admixture of $C_4$ hydrocarbons. The invention comprises passing only a portion of the feed stream through a hydration zone wherein the alcohol is produced. The residual hydrocarbon effluent of the hydration zone and the remaining portion of the $C_4$ feed stream are passed into an etherification zone, which is capable of consuming a greater percentage of the entering isobutylene than is the hydration zone. A further benefit is achieved if the alcohol is dehydrated to produce high purity isobutylene since this reaction is more selective than the "cracking" of the coproduced ether.

One embodiment of the invention may be characterized as a hydrocarbon conversion process which comprises the steps of dividing a feed stream which comprises normal butane, isobutane, and isobutylene into a first portion and a second portion; passing the first portion of the feed stream into a hydration zone wherein isobutylene is reacted with water to produce tertiary butyl alcohol and withdrawing from the hydration zone a first effluent stream comprising isobutylene, isobutane and normal butane and a first product stream comprising tertiary butyl alcohol; and passing the first effluent stream and the second portion of the feed stream into an etherification zone wherein isobutylene is reacted with methanol to produce methyl tertiary butyl ether and withdrawing from the etherification zone a second effluent stream comprising normal butane and isobutane and a second product stream comprising methyl tertiary butyl ether.

DESCRIPTION OF THE DRAWING

A $C_4$ hydrocarbon feed stream comprising a mixture of isobutane, isobutylene and normal butane enters the process through line 1 and is divided into a first portion which is passed into a hydration zone 3 through line 2 and a second portion which continues through line 13. The isobutylene which enters the hydration zone through line 2 is reacted with water entering through line 4 to form tertiary butyl alcohol (TBA) which is separated from the reactants and removed from the hydration zone through line 5. The TBA produced in this manner may be withdrawn from the process as a product stream carried by line 6 or alternatively all or a portion of the TBA produced in the hydration zone may be passed through line 7 into a TBA dehydration zone 8. The dehydration of the TBA results in the release of the isobutylene originally present in the feed stream of line 1, with this isobutylene being removed from the process as a second product stream carried by line 9. Water released in the dehydration zone is recycled through line 10 and admixed with any makeup water from line 11 to form the water stream passed into the hydration zone.

The unreacted portion of the feed stream of line 1 is removed from the hydration zone 3 in line 12, and comprises a mixture of the original hydrocarbons with a reduced but still significant concentration of isobutylene. This stream is combined with the portion of the feed stream carried by line 13 and passed into the etherification zone 15 through line 14. In the etherification zone, the entering $C_4$ hydrocarbons are admixed with methanol from line 16 and contacted with an etherification catalyst to result in the production of methyl tertiary butyl ether (MTBE). The MTBE is removed from the etherification zone as a third product stream carried by line 17. The unreacted hydrocarbons which enter the etherification zone are withdrawn in line 18 as what is sometimes referred to in the art as a $C_4$ raffinate stream and which may be withdrawn from the process through line 19 in total or in part.

In one embodiment of the subject process, all or a portion of the $C_4$ raffinate stream is passed through lines 20 and 32 into a dehydrogenation zone 22. This embodiment may be employed when the material flowing through line 20 has a substantial concentration of isobutane, and results in the conversion of the isobutane flowing through line 32 into a mixture of isobutane and isobutylene which is removed from the dehydrogenation zone in line 23 and passed into an optional isobutylene separation zone illustrated as the deisobutanizer column 24. Preferably this optional column effects the separation of the entering $C_4$ hydrocarbons into an isobutane-rich net overhead stream which is recycled to the dehydrogenation zone through line 26 and a net bottoms stream removed from line 25 which is rich in isobutylene. The isobutylene flowing through line 25 may be processed in one of three alternative ways, which comprise passing the total isobutylene-rich stream into either line 27 or line 28 or splitting the flow of this stream between these two lines. Isobutylene will be caused to pass through line 28 either to increase the production of TBA or to effect a further purification of the isobutylene stream. Isobutylene is caused to pass into the etherification zone 15 through line 27 when it is desired to increase the production of MTBE.

If the $C_4$ stream flowing through line 20 contains appreciable amounts of normal butane, it is preferred that an alternative embodiment of the invention be employed. In this embodiment, all or a portion of the $C_4$ hydrocarbons flowing through line 20 are diverted into line 21 as an isomerization zone feed stream which comprises normal butane and most probably isobutane. The $C_4$ hydrocarbons of line 21 may be augmented by a second $C_4$ feed stream from line 30. The isomerization zone 29 preferably contains a deisobutanizer which receives the feed stream(s) and a reactor effluent stream and which produces separate iso- and normal butane streams. The isobutane so produced and purified is passed into the dehydrogenation zone 22 through line 31.

DETAILED DESCRIPTION

Streams containing a mixture of $C_4$ hydrocarbons are often used as the feedstock in petrochemical or chemical process units. $C_4$ hydrocarbons may be reacted with other hydrocarbonaceous compounds to produce products or intermediate chemicals or may be directly utilized as the feedstock to a polymerization process. These mixed $C_4$'s are often obtained from natural gas or petroleum production or from familiar sources within petroleum refineries such as the gas concentration units of fluidized catalytic cracking units. In recent years there has been increased attention directed to the utilization of isobutylene present in these streams and to the production of additional amounts of isobutylene. For instance, a high purity stream of the isobutylene may be utilized as the feed stream to a polymerization zone producing polyisobutylene. Isobutylene is consumed in the production of methyl tertiary butyl ether (MTBE) which is being used as an anti-knock component in high octane lead-free gasoline. Isobutylene is also utilized in the production of tertiary butyl alcohol (TBA) which may be utilized in gasoline or for the manufacture of methyl methacrylate. The remaining $C_4$ hydrocarbons in the mixed $C_4$ hydrocarbon feed stream may also be utilized for such purposes as the production of polybutylene or as the feed stream to an alkylation zone producing motor fuels.

It is an objective of the subject process to provide an integrated process for the simultaneous production of methyl tertiary butyl ether and tertiary butyl alcohol or high purity isobutylene from a mixed $C_4$ hydrocarbon feed stream. It is another objective of the subject invention to provide an improved process for the separation of isobutylene from a mixed $C_4$ hydrocarbon stream. A further objective of the subject invention is to increase the utilization of isobutylene in a $C_4$ hydrocarbon feed stream charged to an integrated process which produces TBA and MTBE.

The feed stream to the subject process will contain isobutylene and will also contain some amount of many other common $C_4$ hydrocarbons. The feed stream may therefore contain isobutylene, isobutane, normal butane, butene-1 and butene-2. It is preferred that at least 90 mole percent of all compounds in the feed stream contain four carbon atoms per molecule. It is further preferred that the feed stream contains at least 5 mole percent and more preferably at least 10 mole percent isobutylene. It is also preferred that the feed stream is free of butadienes and various compounds which may act as catalyst poisons.

The initial step in the subject process is the division of the $C_4$ hydrocarbon feed stream into two portions having equal compositions. A first portion of the feed stream is passed into a hydration zone wherein a portion of the isobutylene is converted to TBA by reaction with water. The other hydrocarbons in this portion of the feed stream are unaffected by passage through the hydration zone and emerge as a hydrocarbon effluent which is then combined with the second portion of the original $C_4$ feed stream to the process. That is, a portion of the original $C_4$ feed stream bypasses the hydration zone in the subject process. It is preferred that at least 15 mole percent of the original $C_4$ feed stream bypasses the hydration zone in this manner, and the bypassed portion may reach 80 mole percent or more of the original feed stream depending on the desired operation and product mix of the overall process. The second portion of the main feed stream and the $C_4$ hydrocarbons leaving the hydration zone are then passed into an etherification zone either separately or as a commingled admixture. In this zone the very great majority, preferably at least 98–99 mole percent, of the remaining isobutylene is converted into an ether. The other $C_4$ hydrocarbons are removed from the etherification zone as an effluent stream sometimes referred to as the $C_4$ raffinate or recycle stream.

The invention may therefore be broadly characterized as a hydrocarbon conversion process which comprises dividing a feed stream comprising isobutylene and isobutane into a first portion and a second portion; passing the first portion of the feed stream into a hydration zone wherein isobutylene is converted into tertiary butyl alcohol and producing a first product stream comprising tertiary butyl alcohol and a first effluent stream comprising the remaining unconverted isobutylene and the isobutane charged to the hydration zone; and passing the first effluent stream and the second portion of the feed stream into an etherification zone wherein isobutylene is converted into an ether by reaction with an alcohol and thereby producing a second product stream comprising the ether and a second effluent stream comprising isobutane. In a more limited embodiment of the invention, the tertiary butyl alcohol produced in the hydration zone is charged to a dehydration zone wherein it is converted into isobutylene and water. The water may be recycled to the hydration zone and the isobutylene is withdrawn from the process as an additional product stream.

The subject process has basic advantages which it is believed are not present in the prior art processes. First, since the etherification reaction may be quite readily caused to consume essentially all of the available isobutylene, the etherification zone serves to effectively upgrade the isobutylene which is not reacted in the hydration zone. That is, it is possible to quite easily achieve a much higher overall conversion, based on isobutylene disappearance, in an etherification zone than in a hydration zone. The linkage of the two zones as claimed herein therefore results in a much greater utilization of the available isobutylene. A second advantage of the subject process may result when it is desired to produce isobutylene. In this instance the TBA produced in the hydration zone can be charged to a dehydration zone wherein the alcohol is cleaved into isobutylene and water. This dehydration or "cracking" operation is believed in some instances to be slightly more selective than the "cracking" of MTBE produced in the etherification zone. The ability to produce high purity isobutylene by TBA dehydration may therefore be advantageous over a process which must produce the isobutylene from MTBE. A third advantage of the overall process is the flexibility which it allows in choosing the products of the process. For instance, the ratio of ether production to alcohol production may be adjusted by a corresponding adjustment in the volumetric rate of the first portion of the feed stream which is passed into the hydration zone. This flexibility also extends to the amount of isobutylene which may be produced. In this manner the operation of the overall process may be adjusted for variations in product demands or prices.

The various conversion zones utilized in the subject integrated process are all known to those skilled in the art as illustrated by the references set out above. Furthermore there are several alternative designs available for each of these zones. These zones are also the subject of continuing development work which will undoubtedly result in new and improved designs, catalysts and operating techniques. The following description of the various individual zones utilized in the overall process is therefore only intended to illustrate more completely the practice of the subject invention and to describe the presently preferred method of performing the invention, and it is not intended to thereby limit the scope of the subject invention to these particular operational embodiments.

The hydration zone preferably comprises a separate reaction section (reactor) and a reactor effluent separation section which normally comprises at least one fractional distillation column. The conditions employed in the reaction section may include a temperature in the range of about 120°-260° F. (49°-127° C.) A superatmospheric pressure sufficient to maintain liquid phase conditions is preferred, with pressures under 1,000 psig being especially preferred. The reaction section may comprise one or more separate reactors in series flow, with the use of a multi-stage reaction zone having several points of water addition being preferred. The preferred catalysts are solid particles comprising an acidic cation exchange resin, such as a styrene resin, acrylic resin or phenolic resin, which is produced by contacting the resin with a substance which introduces sulfonic acid groups into the resin structure. The preferred resinous particles should have a large surface area and a macroporous structure. Suitable cation exchange resins are presently available commercially.

The effluent of the hydration reaction section is preferably passed into a distillation column in which the effluent is separated into a net bottoms stream which is rich in tertiary butyl alcohol and a net overhead stream which comprises the comparatively inert $C_4$ hydrocarbons, such as the butanes, and the unconsumed isobutylene. Since the overhead stream is to contain isobutylene, the reaction section may be economized or conditions changed to the extent which allows the achievement of the desired partial conversion at the lowest cost. This may allow a reduction in by-product formation. Also, since the complete utilization of the isobutylene is not desired the recycling within the hydration zone of any isobutylene-containing stream such as the overhead material is not required. The net overhead material preferably comprises at least 2 mole percent isobutylene and is charged to the etherification zone. If a high purity ether is desired it is preferred that the net overhead material is treated, as by adsorption or distillation, to reduce any major water concentration prior to the passage of this material into the etherification zone since the added water would produce TBA in the etherification zone. If the product of the etherification zone is to be used as a motor fuel blending stock or in some other application where high purity ethers are not required, then water may be allowed to remain in the net overhead material as the TBA is also suitable as motor fuel.

The dehydration zone can be operated at a wider range of conditions including lower temperatures and pressures. Subatmospheric pressures may be used in the reaction section of the dehydration zone to allow the vaporization of the isobutylene released by the dehydration of the TBA. Temperatures in the reaction section may therefore range from about 68°-212° F. (20°-100° C.) with preferred temperatures being below 170° F. (76° C.) to avoid isobutylene polymerization. A pressure below 150 psig is preferred, with pressures less than 100 psig being especially preferred. The dehydration zone is basically designed to promote the release of isobutylene and water by the same reversible reaction performed in the hydration zone. The same catalysts as employed in the hydration zone may therefore be used in the dehydration reaction section. The reaction section may be a catalyst containing column from which vapors are allowed to pass into an overhead condensing system such as employed in fractional distillation columns. Following a partial condensation, water is separated by decantation from a hydrocarbonaceous phase containing unconverted TBA, which is refluxed back to the reaction section. The water may be returned to the hydration section thus eliminating purification or disposal problems. The uncondensed vapor removed from the overhead separatory vessel comprises the product isobutylene and may be directly withdrawn from the process or may be treated as by low temperature or adsorptive drying.

The $C_4$ hydrocarbon stream removed from the separation section of the hydration zone and the portion of the original feed stream which bypassed the hydration zone are both fed into an etherification zone for the purpose of reacting the isobutylene content of these streams with an alcohol to form an ether. The preferred alcohol has less than four carbon atoms per molecule. This alcohol is preferably methanol, with ethanol being the next preferred. The alcohol can however be chosen from primary and secondary propanol, the various propanols, the dihydroxy alcohols such as ethylene glycol and propylene glycol and other alcohols. The preferred class of alcohols are $C_4$-minus aliphatic monohydroxy alcohols. The majority of the description of the invention is presented in terms of the reaction of isobutylene with methanol since these are the preferred feed materials and this is the commercially predominant reaction. However, it is not intended to thereby lessen the scope of the inventive concept. This is especially true since there have been predictions that the expected large demand for ethers as antiknock additives will lead to the use of large amounts of ethanol produced by fermentation in etherification processes.

Several suitable etherification processes have been described in the available literature, with such processes presently being used to produce MTBE for petrochemical and gasoline additive consumption. The preferred form of the etherification zone is similar to that described in previously cited U.S. Pat. Nos. 4,219,678 and 4,282,389 and also described in a paper delivered by F. Obenaus and W. Droste at the 85th National Meeting of the American Institute of Chemical Engineers in June 1978. In this instance the isobutane or other isoolefin, methanol or other feed alcohol, and a recycle stream containing the product ether, and methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites and various sulfonated resins. The use of a sulfonated solid resin catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions includes a superatmospheric pressure sufficient to maintain the reactants as a liquid phase, generally below about 200 psig, and a temperature between about 30° and about 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily with two reactors. The ratio of feed alcohol to isoolefin should normally be maintained in the broad range 1:1 to 2:1. With the preferred reactants good results are achieved if the ratio of methanol to isobutene is between 1.1:1 and 1.5:1. An excess of methanol above that required to achieve satisfactory conversion at good selectivity should be avoided.

It is preferred that the effluent of the etherification reaction zone is passed into an intermediate point of a fractionation column designed and operated to concentrate unconverted $C_4$ hydrocarbons present in the effluent into a net overhead stream. In the case of isobutene being the isoolefin this column is a deisobutanizer. The net overhead stream of this column becomes the $C_4$ hydrocarbon effluent stream of the etherification zone. This stream is preferably water washed to recover water-soluble compounds such as the methanol if it is withdrawn from the process. Alternatively it may be recycled to produce additional isobutylene as described below. The bottoms stream of this column contains most of the product ether and excess alcohol present in the reaction zone effluent stream and is preferably passed into a second fractionation column. By proper operation of the second column the entering materials may be separated into a net overhead stream which is a recyclable alcohol-ether azeotrope and a bottoms stream of relatively pure product ether which is withdrawn as the product stream of the process. Further details on the separatory method and other aspects of the etherification zone may be obtained from the previously cited references.

The process steps described above comprise the main inventive concept and basic embodiment of the subject invention. They may be practiced as described above without elaboration. In other embodiments of the invention at least a portion of the $C_4$ hydrocarbon effluent stream leaving the etherification zone is processed to produce additional isobutylene which is charged to the hydration and/or the etherification zones. This processing may comprise only the dehydrogenation of isobutane or both the isomerization of normal butane and isobutane dehydrogenation. If both processes are not employed it will be necessary to draw off a portion of the $C_4$ hydrocarbon effluent stream to prevent the buildup of normal butanes within the process.

To convert some of the isobutane present in the etherification zone $C_4$ effluent stream, a portion of this stream, or the effluent of the isomerization zone, or an isobutane-rich stream formed by fractionating either of these two source streams is passed into a butane dehydrogenation reaction zone. As used herein the term "rich" is intended to indicate that the process stream contains at least 55 mole percent of the particular chemical compound or class of compounds which is specified. The dehydrogenation zone will contain a reaction section and associated auxiliary process equipment such as condensers and a vapor-liquid separator which receives the partially condensed reactor effluent stream. A hydrogen-rich gas stream is preferably separated from the liquid condensed from the reactor effluent. A portion of this gas will normally be recycled and the remainder will be drawn off as a net hydrogen product gas stream. The reaction section preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction section. A detailed description of moving bed reactors of this type may be obtained by reference to U.S. Pat. Nos. 3,647,680; 3,706,536; 3,825,116; 3,839,196; 3,839,197; 3,854,887, 3,856,662 and 3,978,150.

The liquid stream withdrawn from the vapor-liquid separator is the effluent stream of the dehydrogenation reaction section. This stream is passed into a fractionation system which preferably contains a single fractionation column referred to herein as a light ends stripping column. For MTBE production this column is designed and operated to eliminate all ethane and lighter boiling components from the net dehydrogenation zone effluent stream. It may also separate some and possibly all of the propylene into the light ends stream removed from this zone. The propylene may result from the dehydrogenation of propane present in the feed stream to the process or from the cracking of butanes during the production of the light ends removed from this zone. The $C_4$ containing bottoms stream of the light ends stripping column may be withdrawn as the dehydrogenation zone effluent stream. It may therefore be passed into the isobutylene consuming zones of the process. In a more limited embodiment the bottoms of the light ends stripping column is passed into a separatory zone wherein the isobutylene is separated from other $C_4$ hydrocarbons to yield a high purity isobutylene which, although it could be withdrawn as an additional product stream, is preferably passed into the etherification and/or hydration zones. A fractionation column may be employed as this separatory zone, but it is preferred that a selective adsorbent retained as a fixed bed in a simulated moving bed separatory process is employed as the separatory zone.

The particular dehydrogenation conditions employed within the reaction zone may vary depending on such factors as the catalyst activity, feed carbon number and the desired conversion. The reaction conditions normally employed for butane dehydrogenation include a temperature of from about 500° to 700° C., a pressure of from 0.5 to about 10 atmospheres and a liquid hourly space velocity of about 1 to 20. The preferred operating temperature will be within the range of from about 550° to 660° C., and the preferred operating pressure is about 0.5 to 2 atmospheres. The preferred butane dehydrogenation catalyst is comprised of a platinum group component, preferably platinum, a tin component and an alkali metal component with a porous inorganic carrier material. Other catalytic compositions may be used within this zone if desired. The preferred catalyst contains an alkali metal component chosen from cesium, rubidium, potassium, sodium, and lithium. The preferred alkali metal is normally chosen from lithium and potassium, with potassium being preferred for isobutane. Another preferred dehydrogenation catalyst comprises approximately equal amounts of an alkali metal and a halogen such as potassium and chlorine in addition to the tin and platinum group components. The preparation and use of dehydrogenation catalysts is well known to those skilled in the art and further details as to suitable catalyst compositions is available in patents and other standard references.

To increase the supply of isobutane available to the dehydrogenation zone and also to convert the nonreactive normal paraffins of the etherification zone effluent stream, all or a portion of the $C_4$ etherification zone effluent stream is preferably passed into a butane isomerization zone. This zone comprises a reactor and auxiliary process equipment such as heaters, condensers, separatory vessels, etc. The isomerization zone preferably also contains a stripping column which eliminates light ends (hydrogen, methane, ethane) from the net effluent of the isomerization zone. With the preferred catalyst, this stripping column will also remove volatile chloride compounds from the isomerization effluent.

The core of the operation of this zone is passage of the sidecut stream through a reactor maintained at butane isomerization-promoting conditions including the presence of an acidic isomerization catalyst. This is normally a relatively low pressure operation performed at a pressure of from about 50 to 600 psig and at an elevated temperature as required by the activity of the catalyst. The average reactant temperature may be as high as 500° C., but is preferably between 100° and 320° C. It is normal practice to pass the butane through the reactor in admixture with between 1 and 10 moles of hydrogen per mole of butane to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired.

The effluent of the isomerization reactor is normally separated into a hydrogen-rich recycle gas which is returned to the reactor and an isomerate-containing liquid stream which is passed into the stripping column. The net hydrocarbon effluent of the isomerization unit is normally a mixture of isobutane and normal butane withdrawn from the stripping column. This stream should contain at least 50 mole percent isobutane. Preferably this stream comprises more than 55 or 60 mole percent isobutane. It is within the scope of the inventive concept that this liquid stream may be fractionated within the isomerization unit in a deisobutanizer column to allow the recycling of normal butanes to the isomerization reactor and the achievement of higher conversion rates. The portion of the etherification zone effluent stream passed into the isomerization zone is then preferably charged to the deisobutanizer column to allow most of its isobutane content to bypass the isomerization zone. Further details on the optional butane isomerization zone of the subject process may be obtained by referring to the previously cited references.

The preferred isomerization-promoting catalyst for use in the isomerization zone comprises a platinum group component and a halogen component supported by an inorganic oxide carrier. The preferred platinum group components are platinum and palladium or a mixture of platinum and palladium, with platinum being especially preferred. A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

We claim as our invention:

1. A hydrocarbon conversion process which comprises the steps of:
   (a) dividing a feed stream comprising isobutylene and isobutane into a first portion and a second portion;
   (b) passing the first portion of the feed stream into a hydration zone wherein isobutylene is converted into tertiary butyl alcohol and producing a first product stream comprising tertiary butyl alcohol and a first effluent stream comprising isobutylene and isobutane; and, (c) passing the first effluent stream and the second portion of the feed stream into an etherification zone wherein isobutylene is converted into an ether by reaction with an alcohol and producing a second product stream comprising the ether and a second effluent stream comprising isobutane.

2. The process of claim 1 further characterized in that the alcohol is methanol and the ether is methyl tertiary butyl ether.

3. The process of claim 1 further characterized in that at least a portion of the tertiary butyl alcohol produced in the hydration zone is dehydrated to produce isobutylene.

4. The process of claim 1 further characterized in that at least a portion of the isobutane present in the second effluent stream is passed into a dehydrogenation zone and converted into isobutylene.

5. The process of claim 4 further characterized in that isobutylene produced in the dehydrogenation zone is passed into the hydration zone.

6. The process of claim 4 further characterized in that isobutylene produced in the dehydrogenation zone is passed into the etherification zone.

7. The process of claim 4 further characterized in that the second effluent stream also comprises normal butane, at least a portion of the second effluent stream is passed into a butane isomerization zone, and isobutane produced in the butane isomerization zone is passed into the dehydrogenation zone and converted into isobutylene.

8. The process of claim 7 further characterized in that isobutylene produced in the dehydrogenation zone is passed into the hydration zone.

9. The process of claim 7 further characterized in that isobutylene produced in the dehydrogenation zone is passed into the etherification zone.

10. A hydrocarbon conversion process which comprises the steps of:

(a) dividing a feed stream which comprises normal butane, isobutane and isobutylene into a first portion and a second portion;

(b) passing the first portion of the feed stream into a hydration zone wherein isobutylene is reacted with water to produce tertiary butyl alcohol and withdrawing from the hydration zone a first effluent stream comprising isobutylene, isobutane and normal butane and a first product stream comprising tertiary butyl alcohol; and, (c) passing the first effluent stream and the second portion of the feed stream into an etherification zone wherein isobutylene is reacted with methanol to produce methyl tertiary butyl ether and withdrawing from the etherification zone a second effluent stream comprising normal butane and isobutane and a second product stream comprising methyl tertiary butyl ether.

11. The process of claim 10 further characterized in that at least a portion of the second effluent stream is passed into a butane isomerization zone comprising a deisobutanizer column, and at least a portion of the isobutane produced in the butane isomerization zone is passed into a dehydrogenation zone and converted into isobutylene.

12. The process of claim 11 further characterized in that isobutylene produced in the dehydrogenation zone is passed into the hydration zone.

13. The process of claim 11 further characterized in that isobutylene produced in the dehydrogenation zone is passed into the etherification zone.

14. The process of claim 11 further characterized in that all of the second effluent stream is passed into the deisobutanizer column of the butane isomerization zone.

15. The process of claim 10 further characterized in that tertiary butyl alcohol produced in the hydration zone is dehydrated to produce isobutylene.

* * * * *